(12) United States Patent
Spohn et al.

(10) Patent No.: US 6,488,661 B1
(45) Date of Patent: *Dec. 3, 2002

(54) PRESSURE CONTROL SYSTEMS FOR MEDICAL INJECTORS AND SYRINGES USED THEREWITH

(75) Inventors: Michael A. Spohn, Butler, PA (US); Keith Callen, Butler, PA (US)

(73) Assignee: Medrad, Inc., Indianola, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/415,445

(22) Filed: Oct. 8, 1999

Related U.S. Application Data

(63) Continuation-in-part of application No. 09/363,483, filed on Jul. 29, 1999.
(60) Provisional application No. 60/094,998, filed on Jul. 31, 1998.

(51) Int. Cl.[7] ................................................ A61M 1/00
(52) U.S. Cl. ....................................... 604/151; 604/152
(58) Field of Search ........................... 604/68, 70, 151, 604/131, 135, 207–210, 72, 134, 218, 228, 187

(56) References Cited

U.S. PATENT DOCUMENTS

| 4,006,736 | A | | 2/1977 | Kranys et al. |
| 4,677,980 | A | | 7/1987 | Reilly et al. |
| 5,300,031 | A | | 4/1994 | Neer et al. |
| 5,383,858 | A | | 1/1995 | Reilly et al. |
| 5,553,524 | A | * | 9/1996 | Fujita |
| 5,637,095 | A | * | 6/1997 | Nason et al. |
| 5,800,388 | A | * | 9/1998 | Schiff et al. ................. 604/500 |
| 6,083,197 | A | * | 7/2000 | Umbaugh .................... 604/68 |

FOREIGN PATENT DOCUMENTS

| DE | 44 28 467 A1 | 2/1996 |
| WO | WO 97/31665 | 4/1997 |

OTHER PUBLICATIONS

International Search Report based on counterpart PCT Application No. PCT/US99/17262.

* cited by examiner

Primary Examiner—Brian L. Casler
Assistant Examiner—Kevin C. Sirmons
(74) Attorney, Agent, or Firm—Gregory L. Bradley; James R. Stevenson (57) ABSTRACT

The present invention provides a pressure control system for an injector. The pressure control system includes a compliant piston or piston extension member that connects to the plunger of an injector-actuated syringe to prevent pressure overshoots when a closed or blocked fluid delivery pathway is encountered during an injection procedure.

18 Claims, 9 Drawing Sheets

SECTION A-A

FIG.6B SECTION A-A

PRESSURE CONTROL SYSTEMS FOR MEDICAL INJECTORS AND SYRINGES USED THEREWITH

CROSS-REFERENCE TO RELATED APPLICATIONS

This application is a continuation-in-part of application Ser. No. 09/363,483, filed on Jul. 29, 1999, which claims priority to Provisional Application Ser. No. 60/094,998, filed on Jul. 31, 1998, the contents of which are hereby incorporated by reference.

FIELD OF THE INVENTION

The present invention relates generally to medical injectors and syringes used therewith and, more particularly, to pressure control systems for injectors.

BACKGROUND OF THE INVENTION

A number of powered injectors and injector-actuated syringes for use in medical procedures such as angiography, computed tomography (CT), ultrasound and magnetic resonance imaging (MRI) have been developed. For example, U.S. Pat. No. 4,006,736 discloses an apparatus for injecting fluid into the vascular system of a human being or an animal. Likewise, U.S. Pat. No. 4,677,980 discloses an angiographic injector including a rotating turret for housing two angiographic syringes in readiness for injection. Furthermore, U.S. Pat. No. 5,383,858 discloses a front-loading injector and a syringe mountable thereon for injection procedures. The disclosures and drawings of U.S. Pat. Nos. 4,006,736, 4,677,980 and 5,383,858 are hereby incorporated by reference.

Syringe-based injection systems are susceptible to maximum pressures that are higher than the desired programmed pressure when the fluid delivery path is closed or becomes blocked during an injection procedure. Fluid delivery paths can become closed or blocked for any number of reasons, including a closed stopcock or kinked tubing along the fluid path.

The programmed maximum pressure may be exceeded in the syringe due to the rapid rise of the fluid pressure in closed or blocked fluid delivery paths. In normal, open fluid path injection procedures, the control systems of conventional injectors are able to detect when the programmed maximum pressure is achieved and take control steps to decrease the injection speed to prevent pressure overshoots. However, the control systems are unable to deactivate or reverse the injector motor without inducing large and undesirable pressure fluctuations in the syringe and associated disposables. Therefore, during a normal injection, the control systems slow the injection as much as possible by terminating the current to the motor at a rapid controlled rate, thereby avoiding the large pressure fluctuations.

Unfortunately, these conventional control systems are unable to manage the problem of higher maximum pressures experienced during a closed or blocked fluid path injection.

In addition, powered injectors typically need to accommodate syringes having varying stiffness properties. For example, powered injectors may use both plastic and glass syringes, while utilizing the same pressure control algorithm.

SUMMARY OF THE INVENTION

The present invention provides pressure control systems that control pressure overshoots in injector-actuated syringes and associated disposables caused by, for example, closed or blocked fluid delivery paths.

Further, the present invention provides pressure control systems for injectors that accommodate syringes having different stiffness properties, such as plastic and glass syringes.

According to a first aspect of the present invention, a pressure control system lowers pressure overshoots in syringes and associated disposables during an inadvertent closed or blocked fluid path injection.

According to a second aspect of the present invention, a pressure control system allows an injector to accommodate syringes having varying stiffness properties, while not increasing pressure overshoots during closed or blocked fluid path injections. For example, the pressure control system allows an injector to accommodate both plastic and glass syringes, while utilizing the same pressure control algorithm.

According to a third aspect of the present invention, a pressure control system correlates stiffness characteristics of one configuration of syringe to those of a different syringe. Therefore, the pressure control system is able to accurately control pressure overshoots incurred during an inadvertent closed fluid path injection on all suitable syringe types.

In one embodiment, the pressure control system comprises a compliant injector piston that engages a plunger on an injector-actuated syringe.

In another embodiment, the pressure control system comprises a compliant piston extension member that is connected to a conventional injector piston and a plunger on an injector-actuated syringe.

The present invention, along with further aspects and attendant advantages, will best be understood by reference to the following detailed description taken in conjunction with the accompanying drawings.

DETAILED DESCRIPTION OF THE INVENTION

When rapid pressure rises occur in injector-actuated syringes and associated disposables, such as during a closed or blocked fluid path injection, the maximum pressure overshoots are a direct function of (1) the kinetic energy associated with the injection speed and pressure, and (2) the stiffness of the injector system and syringe.

The kinetic energy generated during these abnormal blocked fluid path injections is converted into potential energy as the movement of the injector piston decreases and comes to a stop. The kinetic energy is converted to potential energy by storing the energy in the form of pressure and deflection of the system and the syringe.

The syringe stiffness is typically designed by material choice and wall thickness to meet a certain pressure rating. The injector's mechanics typically adjust for or add compliance or increased deflections under loads to decrease the pressure in the syringe by storing more potential energy in terms of deflection and less in the form of pressure. Adding a spring in the mechanics (e.g., in the piston or in the form of a piston extension) with a controlled spring constant will store potential energy in the spring and decrease the maximum pressure for that system during a blocked fluid path injection.

Turning now to the drawings, a preferred embodiment of the pressure control system 20 of the present invention includes a compliant piston extension 22 (which may be delivered in a sealed, plastic package 10) compromised of the following parts as described below.

Urethane Spring (5)

As best shown in FIGS. 1, 2 and 5a–5c, a Shore 95A urethane spring 5 is preferably utilized in the compliant piston extension 22 to store the potential energy generated during the blocked fluid path injection. A standard steel coil spring could also be used, but the urethane spring 5 is preferred due to the large spring constants required, coupled with the fact that a large deflection could possibly exceed the stress limit of the steel used in a coil spring.

Body (1)

As best shown in FIGS. 1, 2 and 3a–3d, the body 1 of the compliant piston extension 22 houses the urethane spring 5, guides the threaded tip (see below) and incorporates a mechanism 1a, including a slot, approximate its rear end 1c for attaching the body member 1 to the piston 51 of the injector 50. In an additional embodiment, a bayonet connection, as shown and described in U.S. Pat. No. 4,677,980, may be used to interconnect the body 1 to the piston 51.

The body 1 is preferably made from Delrin®, which has good mechanical strength and impact resistance, and a low coefficient of friction. Delrin® can be easily cleaned because contrast fluid does not adhere to its surface.

Threaded Tip (7)

As best shown in FIGS. 1, 2 and 4a–4d, the threaded tip 7 transfers the syringe load to the urethane spring 5. The tip member 7 has a flange member 7a and includes a threaded section 7b having threads which directly interface with the syringe plunger. In alternate embodiments, attachment mechanisms other than threads can be used to interconnect the syringe plunger and the tip member 7. For example, a bayonet connection, as shown and described in U.S. Pat. No. 4,677,980, may be used to interconnect the syringe plunger and the tip member 7.

The threaded tip 7 preferably is made from Delrin® for ease of syringe attachment and cleaning, and for its low wear properties.

Foam Filler Ring (6)

As best shown in FIGS. 1, 2 and 6a–6c, the foam (or elastomeric) filler ring 6 resists fluid entry into the spring area and acts as a low-force collapsible zone during the injection. The foam ring 6 also prevents foreign matter from inhibiting deflection during an injection.

Carriage Bolt (8)

Figures 1, 2:
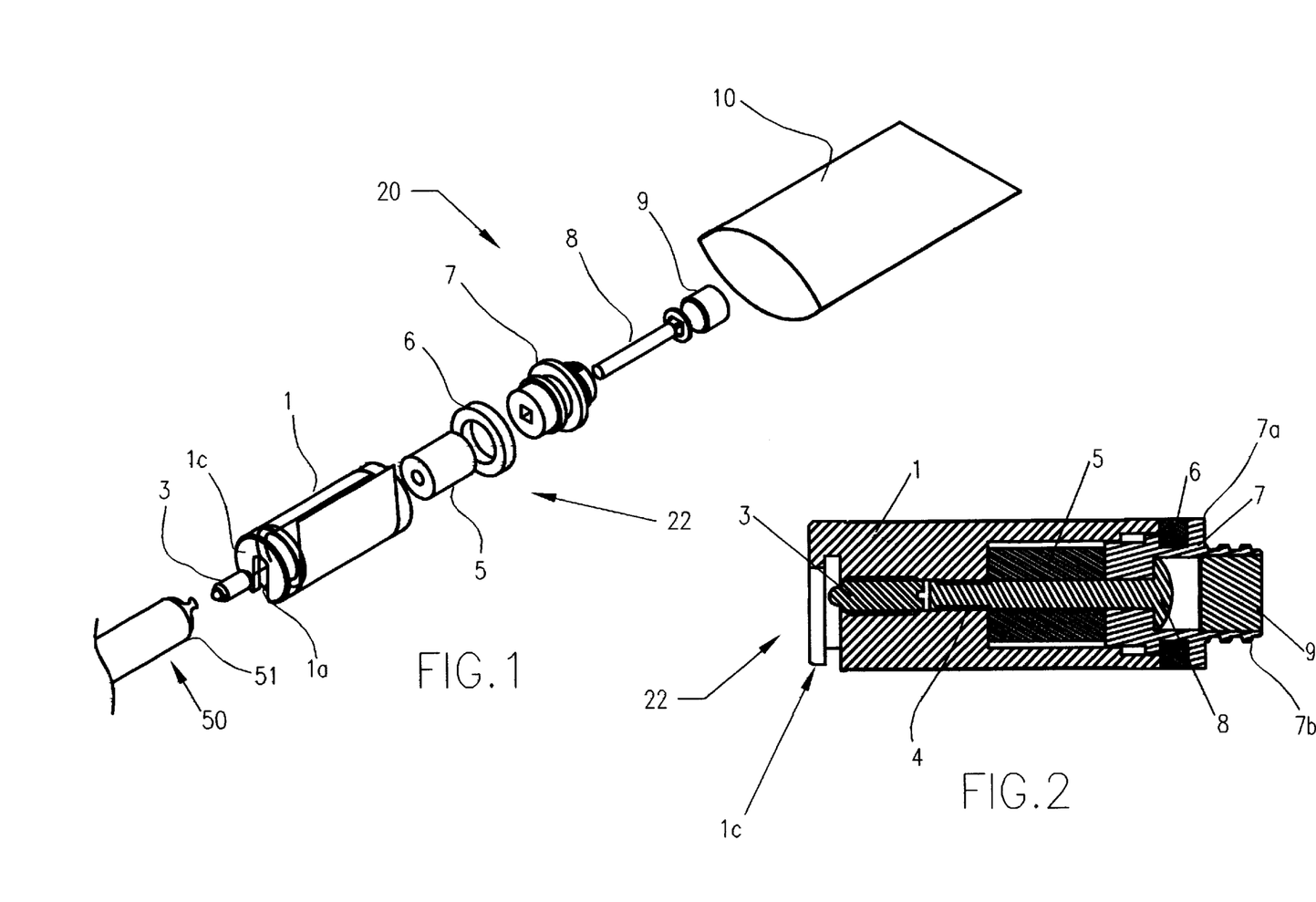
FIG. 1 is an exploded view of a preferred embodiment of the pressure control system of the present invention.
FIG. 2 is a cross-sectional view of the pressure control system shown in FIG. 1.
Figure 3A:
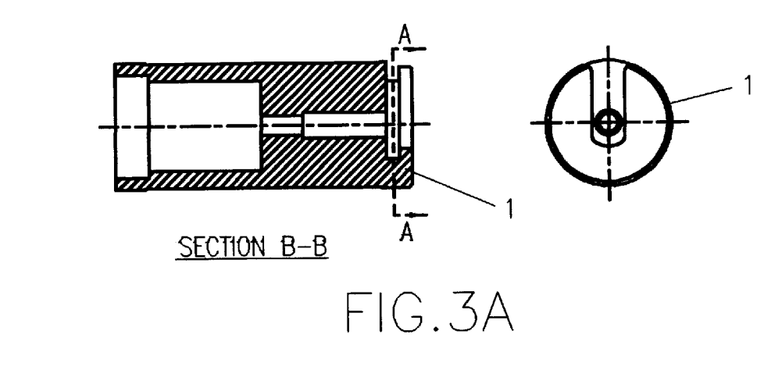
FIGS. 3a–3d are various views of the body of the pressure control system.
Figure 3B:
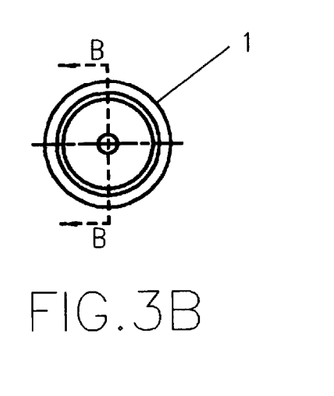
Figure 3C:
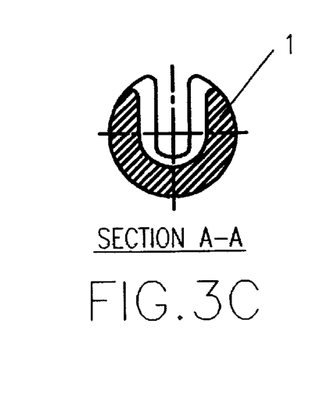
Figure 3D:
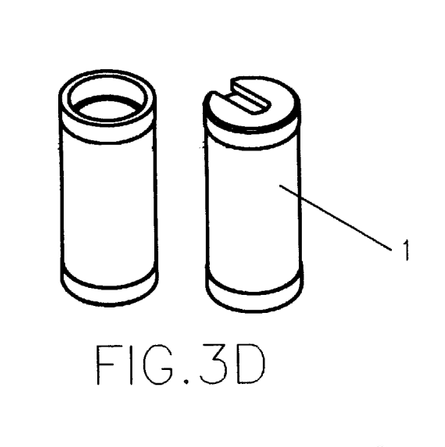
Figure 4A:
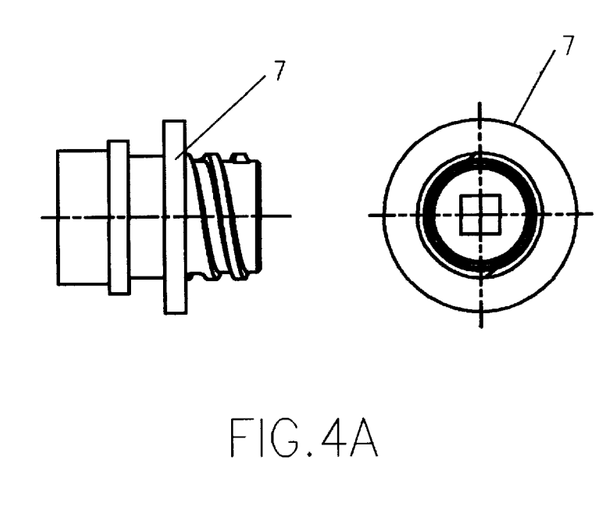
FIGS. 4a–4e are various views of the threaded tip of the pressure control system.
Figure 4B:
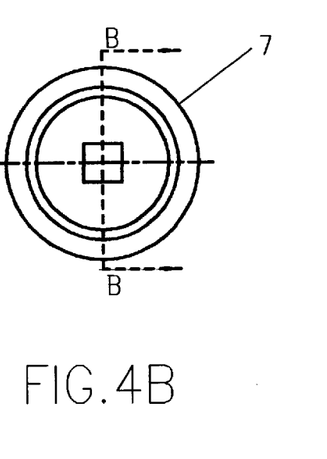
Figure 4C:
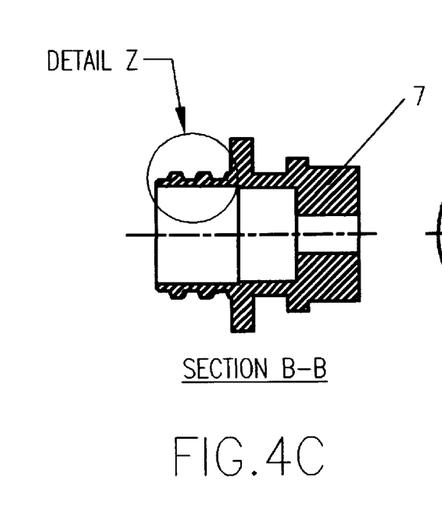
Figure 4D:
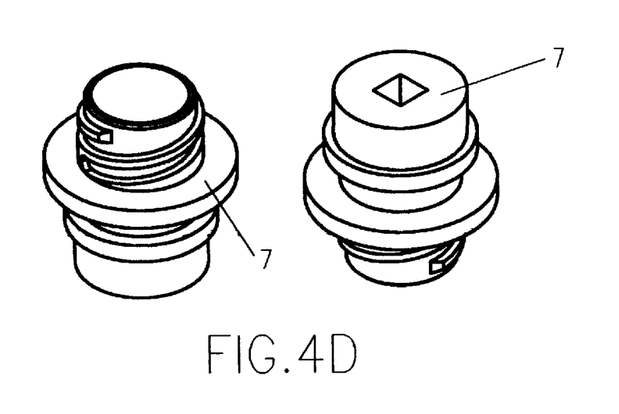
Figure 4E:
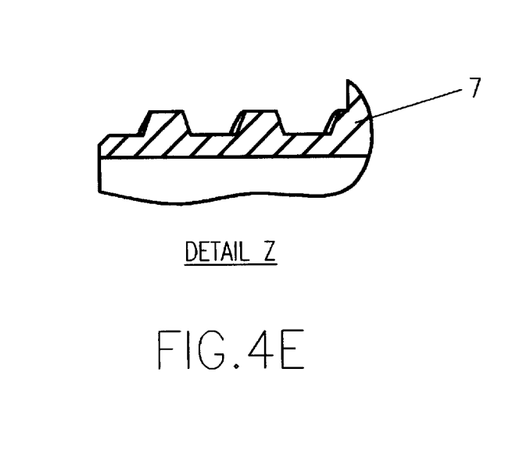
Figure 5A:
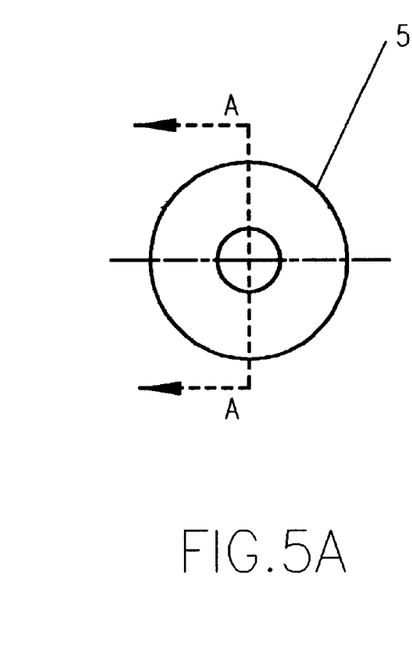
FIGS. 5a–5c are various views of the urethane spring of the pressure control system.
Figure 5B:
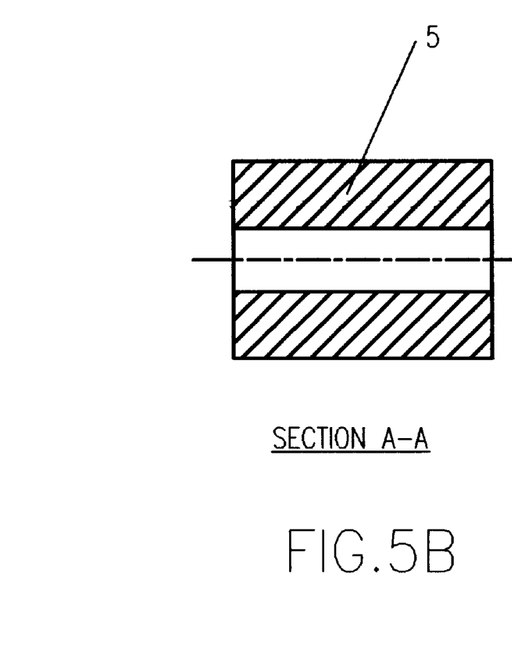
Figure 5C:
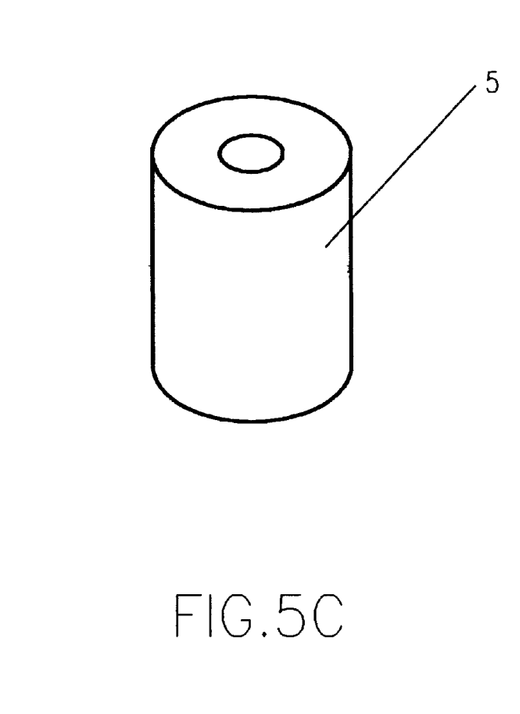
Figure 6A:
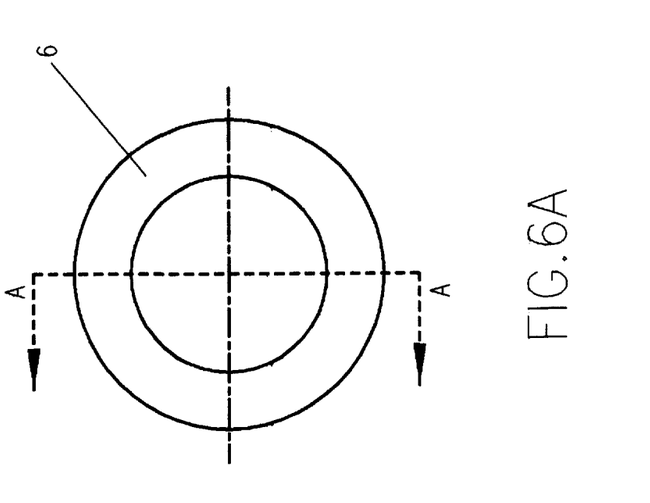
FIGS. 6a–6c are various views of the foam filler ring of the pressure control system.
Figure 6B:
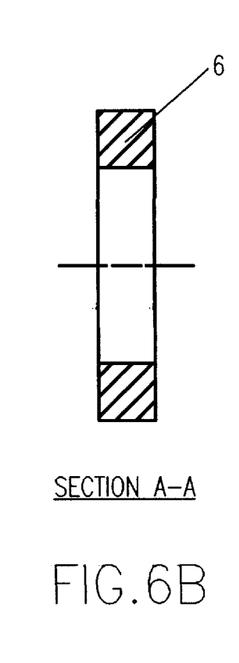
Figure 6C:
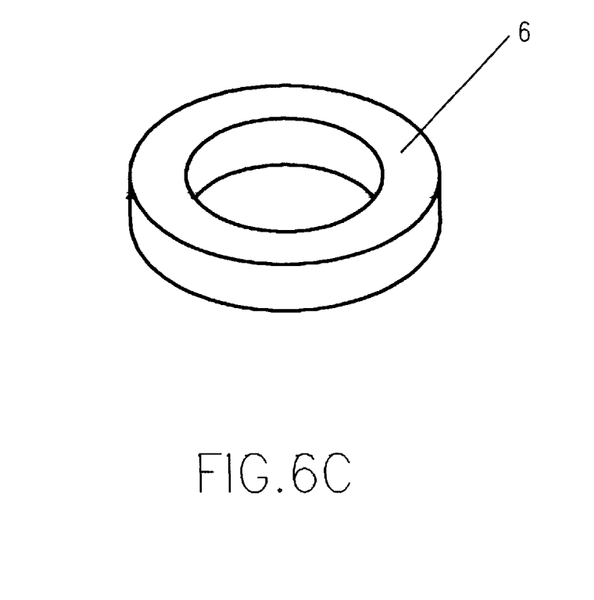
Figure 7A:
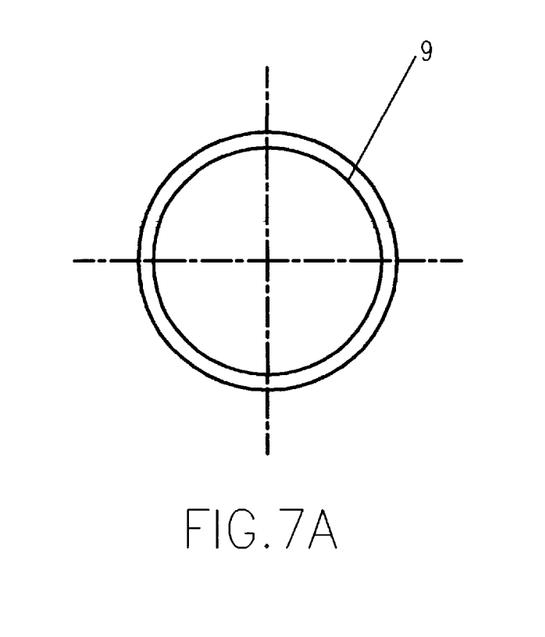
FIGS. 7a–7c are various views of the plug of the pressure control system.
Figure 7B:
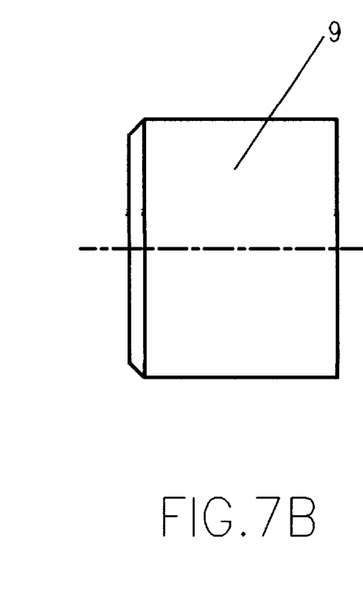
Figure 7C:
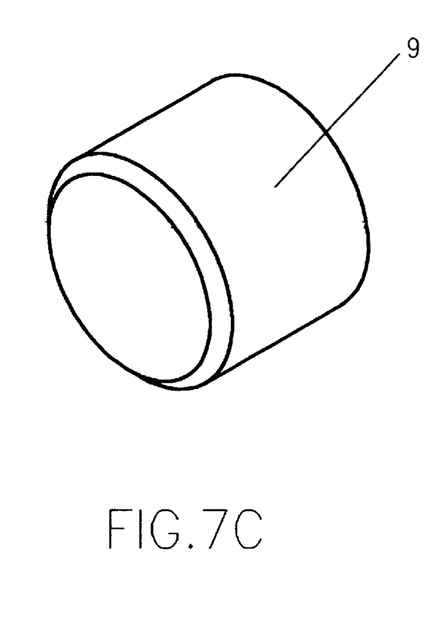

As shown in FIGS. 1 and 2, due to its square-neck design, the carriage bolt 8 holds the components of the compliant piston extension 22 together while at the same time preventing the threaded tip 7 from rotating relative to the body 1 when connecting the syringe thereto. The threads of the carriage bolt 8 are also preferably "loctited" to the body 1 via helicoil 4 to prevent rotation.

In alternate embodiments, fastener members other than the carriage bolt 8 could be used. For example, a stud could be used to accomplish substantially the same function as the bolt 8.

Plug (9)

As best shown in FIGS. 1, 2 and 7a–7c, the plug 9 covers the head of the carriage bolt 8, stiffens the threaded tip 7, and prevents foreign matter from inhibiting deflection during an injection.

Stubby Plunger (3)

As shown in FIGS. 1 and 2, the stubby plunger 3 helps retain the compliant piston extension 22 on the injector piston 51. The plunger 3 seats into a corresponding detent (not shown) in the injector piston 51 and prevents unwanted movement of the compliant extension 22 on the piston 51 during injector head positioning.

Syringe (30)

Figure 8A:
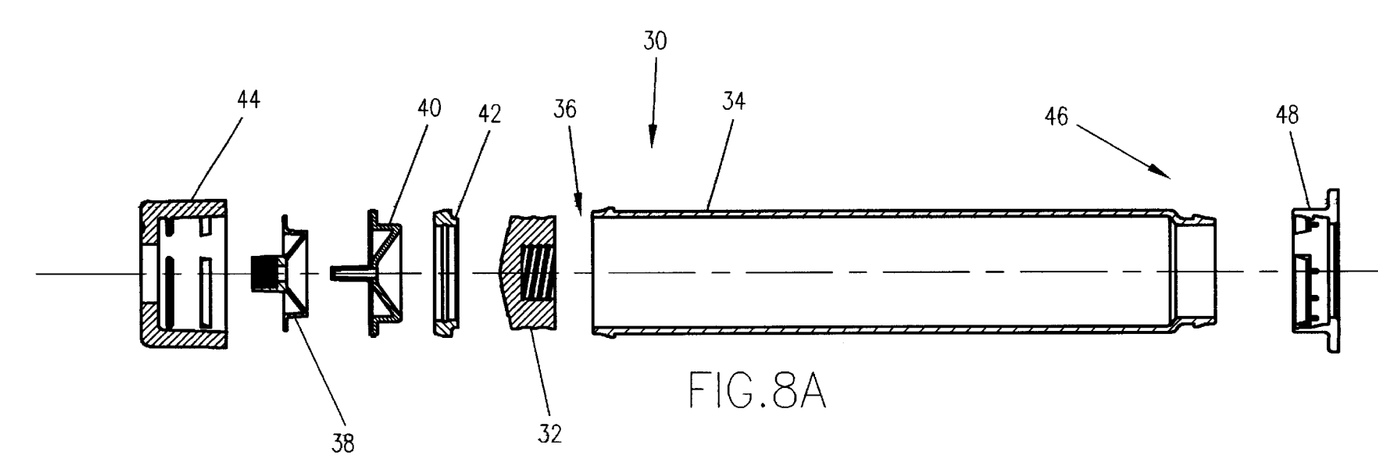
FIGS. 8a and 8b are various views of a syringe usable with the preferred embodiment of the pressure control system of the present invention.
Figure 8B:
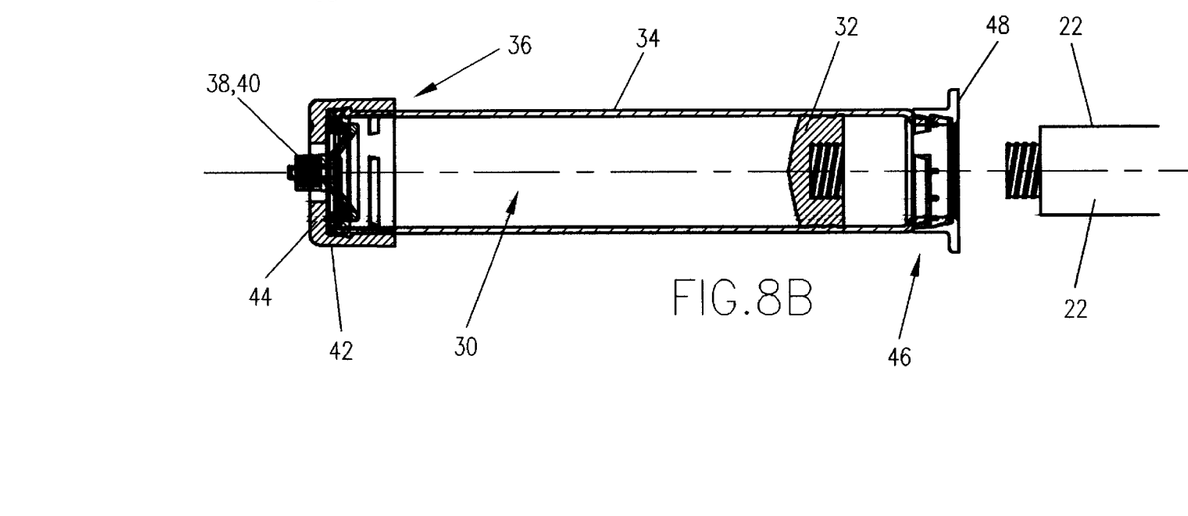

As shown in FIGS. 8a and 8b, a syringe 30 may be used with the compliant piston extension 22 of the present invention. The syringe 30 includes a plunger 32 disposed within a cartridge body 34. The front end 36 of the cartridge body 34 is enclosed by luer lock lids 38, 40, a gasket 42 and a lid holder 44. The rear end 46 of the cartridge body 34 is enclosed by a flange member 48.

As shown, the syringe plunger 32 is internally threaded to mate with external threads on the piston 22. In other embodiments, the syringe plunger 32 could include other attachment mechanisms for interconnecting the syringe plunger 32 and the piston 22. For example, as shown in U.S. Pat. No. 4,677,980, the syringe plunger 32 may include hook or lug members (not shown) extending rearwardly therefrom for connection to a flange member extending from the piston 22.

Figure 9A:
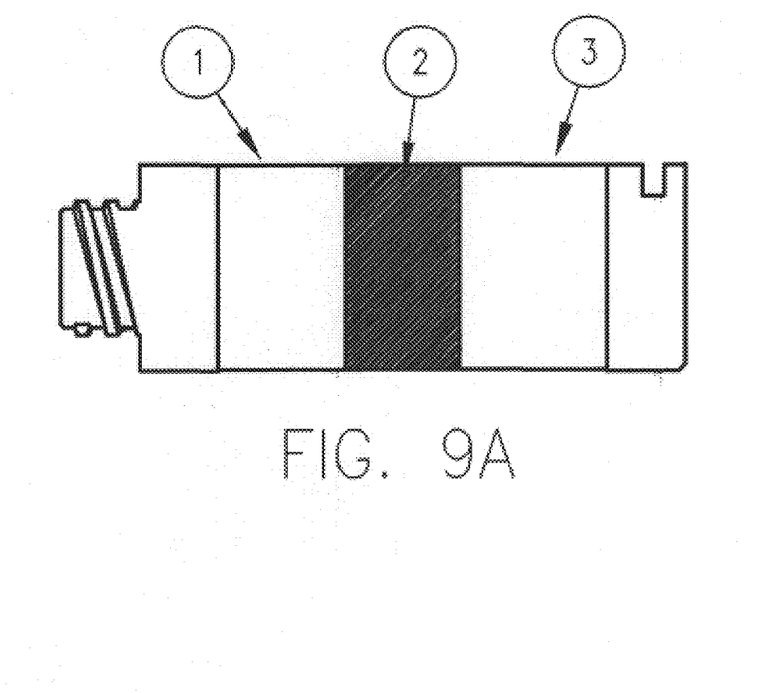
FIGS. 9a–9c are views of an alternate embodiment of the pressure control system of the present invention.
Figure 9B:
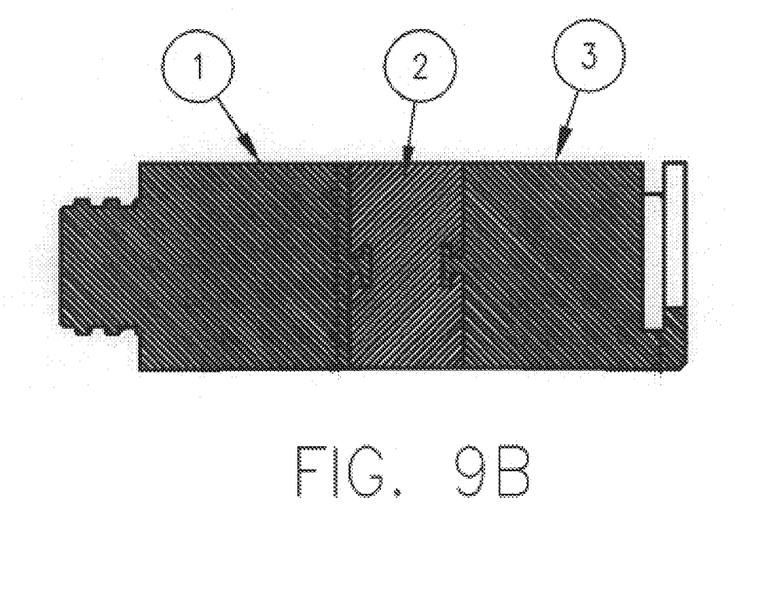
Figure 9C:
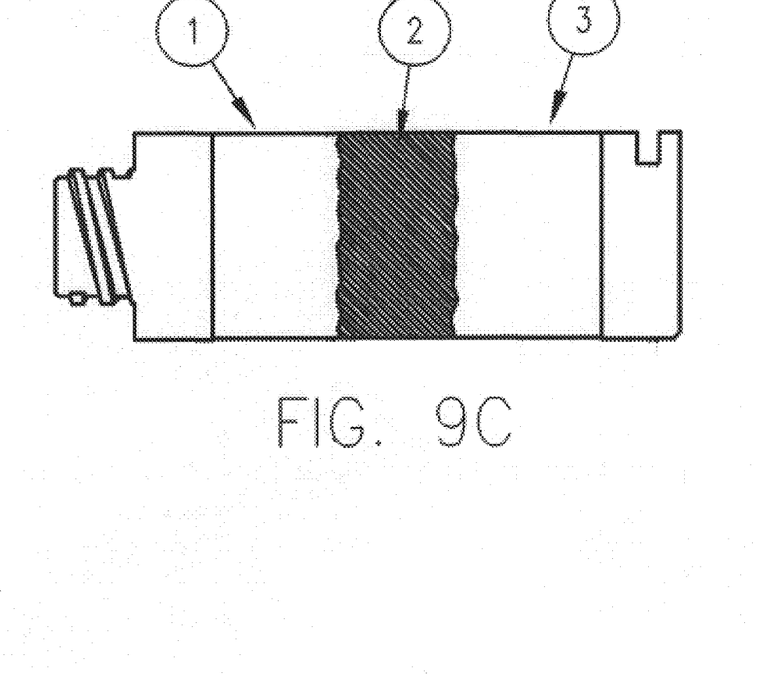
Figure 10:
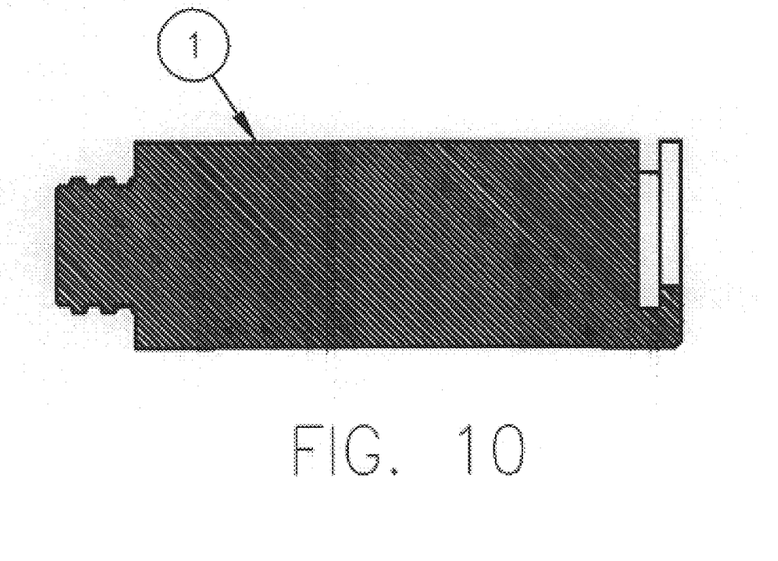
FIG. 10 is a cross-sectional view of another alternate embodiment of the pressure control system of the present invention.

Alternate embodiments of the pressure control system of the present invention are shown in FIGS. 9 and 10. In a first alternate embodiment, as shown in FIGS. 9a–9c, the compliant piston extension 22 may be manufactured from a mold and/or a casting in three or more sections. For example, sections 1 and 3 may be formed from a hard durometer plastic material and section 2 may be formed from an elastomeric material or a soft durometer plastic material. In addition, the sections may be connected or affixed together by any suitable means, including ultrasonic welding, adhesion or gluing, molecular bonding, mechanical interlocking, or any combination thereof.

In the embodiment of FIG. 9a, sections 1–3 may be connected together by gluing or ultrasonic welding. As shown in FIG. 9b, a mechanical interlock may be used to interconnect sections 1–3. Further, as shown in FIG. 9c, the piston extension 22 may be cast as one piece, where the individual sections are cast in order from section 1 to section 3 or from section 3 to section 1. In the embodiment of FIG. 9c, sections 1–3 may be considered to be molecularly bonded.

Additionally, with respect to the embodiments of FIGS. 9a–9c, the desired spring constant of the piston extension 22 can be achieved by, for example, varying the dimensions of section 2 therein.

Further, it is contemplated that sections 1 and/or 3 above may be modified as necessary to mate with corresponding members on a syringe plunger and an injector piston or drive member.

As shown in FIG. 10, in a second alternate embodiment, the entire piston extension 22 (shown also as section 1) may be cast from an elastomeric material or a soft durometer plastic material. In this embodiment, the desired spring constant can be achieved by varying the dimension of section 1. For example, material may be removed from section 1 to decrease the stiffness of the piston extension 22. Likewise, material may be added to section 1 to increase the stiffness of the piston extension 22.

EXAMPLE

The preferred embodiment of the compliant piston extension 22 of the present invention is specifically designed to reduce the set pressure overshoot in a 100 ml glass syringe during a blocked fluid path injection. Specifically, the pressure overshoot was required to be reduced to at least the same pressure level experienced by a 100 ml plastic syringe.

The 100 ml glass syringe was measured to be 28% stiffer than the 100 ml plastic syringe. This 28% stiffness difference was the main cause for the higher pressure overshoots on injectors using the 100 ml glass syringe. Therefore, the compliant piston extension 22 (which was used in conjunction with the 100 ml glass syringe during an injection) incorporated a built-in stiffness constant to make the 100 ml glass syringe appear to the injector to be as stiff as or less stiff than the 100 ml plastic syringe. The stiffness constant or spring constant of the compliant piston extension 22 was calculated from the following relationship of springs in series:

$$1/K_{Plastic} = 1/K_{Glass} + 1/K_{Extension}$$

The urethane spring 5 for this design performed within the range of 2065 lb./in to 6384 lb./in. The high end of the range was determined from the above equation and the measured stiffness of the syringes. The low end was determined from the high pressure specification for the injector divided by the deflection available in the extension.

In the preferred embodiment described above, the pressure control system 20 has been described in terms of a piston extension 22 that connects to the piston 51 of an injector 50.

However, it is specifically contemplated that the pressure control system 20 and the piston extension 22 can be integrated into the injector piston 51.

It should be appreciated that the present invention, including the pressure control system 20 and the piston extension 22, may be configured as appropriate for the application. The embodiments and example described above are to be considered in all respects only as illustrative and not restrictive.

What is claimed is:

1. An injector for use with a syringe comprising a plunger, the injector comprising:
   a piston; and
   a pressure control system removably connected to the piston and adapted to engage the plunger of the syringe, the pressure control system comprising:
   a spring member operable to adjust for pressure increases in the syringe;
   a tip member operably associated with the spring member, the tip member comprising a first end having an attachment member, the attachment member having a threaded section for engaging mating threads of the plunger of the syringe; and
   a body member operably associated with the spring member, the body member comprising a rear end that removably connects to the piston,
   wherein the spring member is disposed between the body member and the tip member.

2. The injector of claim 1 wherein the rear end of the body member comprises a plunger member for connecting the body member to the piston.

3. An injector for use with a syringe comprising a plunger, the injector comprising:
   a piston comprising:
   a pressure control system adapted to engage the plunger of the syringe, the pressure control system comprising:
   a spring member operable to adjust for pressure increases in the syringe;
   a tip member operably associated with the spring member, the tip member comprising a first end having an attachment member, the attachment member having a threaded section for engaging mating threads of the plunger of the syringe; and
   a body member operably associated with the spring member, the body member comprising a rear end that removably connects to the piston,
   wherein the spring member is disposed between the body member and the tip member.

4. The injector of claim 3 wherein the rear end of the body member comprises a plunger member for connecting the body member to the piston.

5. An injector for use with a syringe comprising a plunger, the injector comprising:
   a piston; and
   a pressure control system removably connected to the piston and adapted to engage the plunger of the syringe, the pressure control system comprising:
   a spring member operable to adjust for pressure increases in the syringe, the spring member comprising a urethane spring;
   a tip member operably associated with the spring memer, the tip member comprising a first end having an attachment member that engages the plunger of the syringe; and
   a body member operably associated with the spring member, the body member comprising a rear end that removably connects to the piston;
   wherein the spring member is disposed between the body member and the tip member.

6. An injector for use with a syringe comprising a plunger, the injector comprising:
   a piston; and
   a pressure control system removably connected to the piston and adapted to engage the plunger of the syringe, the pressure control system comprising:
   a spring member operable to adjust for pressure increases in the syringe;
   a tip member operably associated with the spring member, the tip member comprising (i) a first end having an attachment member that engages the plunger of the syringe and (ii) at least one flange member extending radially therefrom;
   a body member operably associated with the spring member, the body member comprising (i) a rear end that removably connects to the piston and (ii) at least one wall member extending forwardly therefrom with the spring member being retained therein between the body member and the tip member; and
   a ring disposed between the at least one wall member of the body member and the at least one flange member of the tip member;

wherein the spring member is disposed between the body member and the tip member.

7. The injector of claim 6 wherein the ring is formed of foam.

8. An injector for use with a syringe comprising a plunger, the injector comprising:
a piston; and
a pressure control system removably connected to the piston and adapted to engage the plunger of the syringe, the pressure control system comprising:
a spring member operable to adjust for pressure increases in the syringe;
a tip member operably associated with the spring member, the tip member comprising a first end having an attachment member that engages the plunger of the syringe;
a body member operably associated with the spring member, the body member comprising a rear end that removably connects to the piston; and
a fastener member disposed through a bore defined in each of the body member, the tip member and the spring member for fastening the members together;
wherein the spring member is disposed between the body member and the tip member.

9. The injector of claim 8 wherein the fastener member comprises a bolt.

10. The injector of claim 8 further comprising a plug member disposed within the bore of the tip member, the plug member operable to stiffen the tip member.

11. An injector for use with a syringe comprising a plunger, the injector comprising:
a piston; and
a pressure control system removably connected to the piston and adapted to engage the plunger of the syringe, the pressure control system comprising:
a spring member operable to adjust for pressure increases in the syringe;
a tip member operably associated with the spring member, the tip member comprising a first end having an attachment member that engages the plunger of the syringe;
a body member operably associated with the spring member, the body member comprising a rear end that removably connects to the piston; and
a plunger member at least partially disposed in a bore formed in the body member, the plunger member operable to engage the piston of the injector to retain the body member thereon;
wherein the spring member is disposed between the body member and the tip member.

12. An injector for use with a syringe comprising a plunger, the injector comprising:
a piston comprising:
a pressure control system adapted to engage the plunger of the syringe, the pressure control system comprising:
a spring member operable to adjust for pressure increases in the syringe, the spring member comprising a urethane spring;
a tip member operably associated with the spring member, the tip member comprising a first end having an attachment member that engages the plunger of the syringe; and
a body member operably associated with the spring member, the body member comprising a rear end that removably connects to the piston,
wherein the spring member is disposed between the body member and the tip member.

13. An injector for use with a syringe comprising a plunger, the injector comprising:
a piston comprising:
a pressure control system adapted to engage the plunger of the syringe, the pressure control system comprising:
a spring member operable to adjust for pressure increases in the syringe;
a tip member operably associated with the spring member, the tip member comprising (i) a first end having an attachment member that engages the plunger of the syringe and (ii) at least one flange member extending radially therefrom;
a body member operably associated with the spring member, the body member comprising (i) a rear end that removably connects to the piston and (ii) at least one wall member extending forwardly therefrom with the spring member being retained therein between the body member and the tip member; and
a ring disposed between the at least one wall member of the body member and the at least one flange member of the tip member;
wherein the spring member is disposed between the body member and the tip member.

14. The injector of claim 13 wherein the ring is formed of foam.

15. An injector for use with a syringe comprising a plunger, the injector comprising:
a piston comprising:
a pressure control system adapted to engage the plunger of the syringe, the pressure control system comprising:
a spring member operable to adjust for pressure increases in the syringe;
a tip member operably associated with the spring member, the tip member comprising a first end having an attachment member that engages the plunger of the syringe;
a body member operably associated with the spring member, the body member comprising a rear end that removably connects to the piston, and
a fastener member disposed through a bore defined in each of the body member, the tip member and the spring member for fastening the members together;
wherein the spring member is disposed between the body member and the tip member.

16. The injector of claim 15 wherein the fastener member comprises a bolt.

17. The injector of claim 15 further comprising a plug member disposed within the bore of the tip member, the plug member operable to stiffen the tip member.

18. An injector for use with a syringe comprising a plunger, the injector comprising:
a piston comprising:
a pressure control system adapted to engage the plunger of the syringe, the pressure control system comprising:
a spring member operable to adjust for pressure increases in the syringe;
a tip member operably associated with the spring member, the tip member comprising a first end having an attachment member that engages the plunger of the syringe;
a body member operably associated with the spring member, the body member comprising a rear end that removably connects to the piston, and
a plunger member at least partially disposed in a bore formed in the body member, the plunger member operable to engage the piston of the injector to retain the body member thereon;
wherein the spring member is disposed between the body member and the tip member.

* * * * *